United States Patent
Mellott et al.

(10) Patent No.: US 10,246,681 B2
(45) Date of Patent: Apr. 2, 2019

(54) REPROGRAMMING OF HUMAN WHARTON'S JELLY CELLS TO PRODUCE HAIR CELLS

(71) Applicant: The University of Kansas, Lawrence, KS (US)

(72) Inventors: Adam J Mellott, Lawrence, KS (US); Michael Detamore, Lawrence, KS (US); Hinrich Staecker, Leawood, KS (US)

(73) Assignee: The University of Kansas, Lawrence, KS (US)

( * ) Notice: Subject to any disclaimer, the term of this patent is extended or adjusted under 35 U.S.C. 154(b) by 41 days.

(21) Appl. No.: 15/353,244

(22) Filed: Nov. 16, 2016

(65) Prior Publication Data

US 2017/0067018 A1 Mar. 9, 2017

Related U.S. Application Data

(62) Division of application No. 14/698,157, filed on Apr. 28, 2015, now Pat. No. 9,512,400.

(60) Provisional application No. 61/985,075, filed on Apr. 28, 2014.

(51) Int. Cl.
*A61K 35/30* (2015.01)
*C12N 15/113* (2010.01)
*C12N 5/0793* (2010.01)

(52) U.S. Cl.
CPC .............. *C12N 5/062* (2013.01); *A61K 35/30* (2013.01); *C12N 15/113* (2013.01); *C12N 2310/14* (2013.01); *C12N 2310/51* (2013.01); *C12N 2506/025* (2013.01); *C12N 2510/00* (2013.01); *C12N 2533/90* (2013.01)

(58) Field of Classification Search
CPC ...... A61K 35/30; C12N 5/062; C12N 15/113; C12N 2506/025; C12N 2510/00; C12N 2533/90

See application file for complete search history.

(56) References Cited

U.S. PATENT DOCUMENTS

2005/0287127 A1 12/2005 Li et al.
2009/0098093 A1* 4/2009 Edge ..................... C12N 5/0627
424/93.7

FOREIGN PATENT DOCUMENTS

WO 2011/153348 A2 12/2011
WO WO 12/103012 * 8/2012

OTHER PUBLICATIONS

Devarajan et al, Cellular Reprogramming 15(1): 43-54, 2013.*
Santi et al, JARO 14:3-15, 2013; available online Oct. 20, 2012.*
Kopke et al, Am. J. Otology 18: 559-571, 1997.*
Uygun et al, Nature Medicine 16(17): 814-821, 2010.*
Taylor, Curr. Op. Biotechnol. 20: 598-605, 2009.*
Parker et al, Hearing Research 232: 29-43, 2007.*
Devarajan, K., Forrest, M. L., Detamore, M. S., & Staecker, H. (2013). Adenovector-Mediated Gene Delivery to Human Umbilical Cord Mesenchymal Stromal Cells Induces Inner Ear Cell Phenotype. Cellular Reprogramming, 15(1), 43-54. doi:10.1089/ml1.2011.0097.
Souaze et al. (Feb. 2013). Differential Roles of Hath 1, MUC2 and P27Kip1 in Relation with Gamma-Secretase Inhibition in Human Colonic Carcinomas: A translational Study. PLOS One 8(2):e55904; pp. 1-11.
Devarajan, K., Staecker, H., & Detamore, M. S. (2011). A Review of Gene Delivery and Stem Cell Based Therapies for Regenerating Inner Ear Hair Cells. Journal of Functional Biomaterials, 2, 249-270. doi:10.3390/jfb2030249.
Sol Collado et al. (Oct. 2008). Recent advances in hair cell regeneration research. Curr. Opin. Otolaryngol. Head Neck Surg. 16(5):465-471. doi:10.1097/MOO.0b013e32830f4ab5.
Mellott, A. J., Devarajan, K., Shinogle, H. E., Moore, D. S., Talata, Z., Laurence, J. S., . . . Detamore, M. S. (2015). Nonviral Reprogramming of Human Wharton's Jelly Cells Reveals Differences Between ATOH1 Homologues. Tissue Engineering: Part A, 21, 1795-1809. doi:10.1089/ten.tea.2014.0340.
Kim Baker, Douglas E. Brough and Hinrich Staecker, Repair of the Vestibular System Va Adenovector Delivery of Atoh 1: A Potential Treat for Balance Disorders, Adv Otorhinolaryngol. Basel, Karger, 2009, vol. 66, pp. 52-63, Ryan AF (ed): Gene Therapy of Cochlear Deafness. University of Maryland School of Medicine, Baltimore, MD., GenVec Inc., Gaithersburg, Md., and University of Kansas School of Medicine, Kansas City, Kans., USA.
Tiantian Cai, Andrew K. Groves, The Role of Atonal Factors in Mechanosensory Cell Specification and Function, Received: Jul. 7, 2014 /Accepted: Oct. 7, 2014, Springer Science+Business Media New York 2014, Mol Neurobiol, DOI 10.1007/s12035-014-8925-0.

(Continued)

*Primary Examiner* — Kevin K Hill
(74) *Attorney, Agent, or Firm* — Maschoff Brennan

(57) ABSTRACT

A method of transforming human cells into mechanosensory hair cells (MHCs), such as inner hear hair cells in the cochlea and vestibular organs, can include: causing human Wharton's jelly cells (hWJCs) to increase expression of or biological function of HATH1 so as to transform the hWJCs into MHCs. The method can include; administering a nucleic acid that encodes HATH1 to the hWJCs; causing inhibited expression of or biological function of HES1 and/or HES5 in the hWJCs; administering a nucleic acid that inhibits HES1 and/or a nucleic acid that inhibits HES5 to the hWJCs; causing inhibited expression of or biological function of HES1 and/or HES5 in the WJCs by administering a nucleic acid that inhibits HES1 and/or a nucleic acid that inhibits HES5; nucleic acids are administered includes a sequence of SEQ ID NO: 2, SEQ ID NO: 3, and/or SEQ ID NO: 4.

17 Claims, 2 Drawing Sheets

Specification includes a Sequence Listing.

(56) References Cited

OTHER PUBLICATIONS

Brandon C. Cox, Renjie Chai, Anne Lenoir, Zhiyong Liu, Lingli Zhang, Duc-Huy Nguyen, Kavita Chalasani, Katherine A. Steigelman, Jie Fang, Alan G. Cheng and Jian Zuo, Spontaneous Hair Cell Regeneration in the Neonatal Mouse Cochlea in Vivo, © 2014. Published by The Company of Biologists Ltd | Development (2014) 141, 816-829 doi:10.1242/dev.103036.
Shi-Ming Yang, Wei Chen, Wei-Wei GUO1, Shuping Jia, Jian-He Sun, Hui-Zhan Liu, Wie-Yen Young, David Z. Z. He, Regeneration of Stereocilia of Hair Cells by Forced Atoh1 Expression in the Adult Mammalian Cochlea, www.plosone.org, Received Jun. 21, 2012; Accepted Aug. 29, 2012; Published Sep. 27, 2012, Sep. 2012, vol. 7, ssue 9, e46355.
Xiaoping Du, Wei Li , Xinsheng Gao, Matthew B. West, W. Mark Saltzman C, Christopher J. Cheng C, Charles Stewart, Jie Zheng, Weihua Cheng, Richard D. Kopke, Regeneration of mammalian cochlear and vestibular hair cells through Hes1/Hes5 modulation with siRNA, Contents lists available at SciVerse ScienceDirect, Hearing Research, journal homepage: www.elsevier.com/locate/heares, X. Du et al. / Hearing Research 304 (2013) 91e110.
Ryoukichi Ikeda, Kwang Pak, Eduardo Chavez, Allen F. Ryan, Transcription Factors with Conserved Binding Sites Near ATOH1 on the POU4F3 Gene Enhance the Induction of Cochlear Hair Cells, Received: Mar. 5, 2014 /Accepted: Jun. 22, 2014, Springer Science+ Business Media New York (outside the USA) 2014.
Masahiko Izumikawa, Ryosei Minoda, Kohei Kawamoo, Karen A Abrashkin, Donald L Swiderski, David F Dolan, Douglas E Brough & Yehoash Raphael, Auditory Hair Cell Replacement and Hearing Improvement by Atoh1 Gene Therapy in Deaf Mammals, 2005 Nature Publishing Group http://www.nature.com/naturemedicine, Published online Feb. 13, 2005; doi:10.1038/nm1193, vol. 11, No. 3, Mar. 2005, pp. 271-276.
Israt Jahan, Ning Pan, Jennifer Kersigo, Bernd Fritzsch, Beyond Generalized Hair Cells: Molecular Cues for Hair Cell Types, University of Iowa, Department of Biology, College of Liberal Arts and Sciences, 143 BB, Iowa City, IA 52242, USA, journal homepage: www.elsevier.com/locate/heares, Hearing Research 297 (2013) 30e41.
Jae Yun Jung, Matt R. Avenarius, Swetlana Adamsky, Evgenia Alpert, Elena Feinstein and Yehoash Raphael, siRNA Targeting Hes5 Augments Hair Cell Regeneration in Aminoglycoside-damaged Mouse Utricle, 1KHRI, Otolaryngology, Head & Neck Surgery, publication Feb. 26, 2013. doi:10.1038/mt.2013.18, www.moleculartherapy.org vol. 21 No. 4, 834-841 Apr. 2013.
Kohei Kawamoto, Shin-Ichi Ishimoto, Ryosei Minoda, Douglas E. Brough, and Yehoash Raphael, Math1 Gene Transfer Generates New Cochlear Hair Cells in Mature Guinea Pigs in Vivo, The Journal of Neuroscience, Jun. 1, 2003 • 23(11):4395-4400 • 4395.
Shannon Kraft, MD; Chi Hsu; Douglas E. Brough, PhD; Hinrich Staecker, MD, PhD, Atoh1 Induces Auditory Hair Cell Recovery in Mice After Ototoxic Injury, Laryngoscope, 123:992-999, 2013.
Kunio Mizutari, Masato Fujioka, Makoto Hosoya, Naomi Bramhall, Hirotaka James Okano, Hideyuki Okano, and Albert S.B. Edge, Notch Inhibition Induces Cochlear Hair Cell Regeneration and Recovery of Hearing after Acoustic Trauma, Neuron 77, 58-69, Jan. 9, 2013 ª2013 Elsevier Inc.
Joanna F. Mulvaney, Yutaka Amemiya, Stephen D. Freeman†, Raj K. Ladher and Alain Dabdoub, Molecular cloning and functional characterisation of chicken Atonal homologue 1: A comparison with human Atoh1, Biol. Cell (2015) 107, 41-60 DOI: 10.1111/boc.201400078.
Hinrich Staecker, MD, PhD; Christina Schlecker, MD; Shannon Kraft, MD; Mark Praetorius, MD; Chi Hsu; Douglas E. Brough, PhD, Optimizing Atoh1-induced Vestibular Hair Cell Regeneration, Laryngoscope, 124:S1-S12, 2014.
Juanmei Yang, Ning Cong, Zhao Han, Yibo Huang, Fanglu Chi, Ectopic Hair Cell-Like Cell Induction by Math1 Mainly Involves Directtransdifferentiation in Neonatal Mammalian Cochlea, 0304-3940/$—see front matter © 2013 Elsevier Ireland Ltd. All rights reserved., http://dx.doi.org/10.1016/j.neulet.2013.04.053, J. Yang et al. / Neuroscience Letters 549 (2013) 7-11.

* cited by examiner

REPROGRAMMING OF HUMAN WHARTON'S JELLY CELLS TO PRODUCE HAIR CELLS

CROSS-REFERENCE

This patent application claims priority to U.S. Provisional 61/985,075 filed Apr. 28, 2014, which provisional application is incorporated herein by specific reference in its entirety.

GOVERNMENT RIGHTS

This invention was made with government support under R01 AR056347-01 awarded by the NIH. The government has certain rights in the invention.

This patent application is a divisional application of U.S. patent application Ser. No. 14/698,157 filed Apr. 28, 2015, which claims priority to U.S. Provisional 61/985,075 filed Apr. 28, 2014, which applications are incorporated herein by specific reference in their entirety.

SEQUENCE LISTING

The instant application contains a Sequence Listing which has been submitted electronically in ASCII format and is hereby incorporated by reference in its entirety. Said ASCII copy, created on Apr. 28, 2015, is named K1262.10052US01_SL.txt and is 9,531 bytes in size.

BACKGROUND

Mechanosensory hair cells (MHCs) facilitate hearing and balance in the cochlea and vestibular organs, respectively. MHCs are susceptible to damage from antibiotics, aging, wear and tear, noise-induced stress, and different types of infections. Hearing loss occurs when MHCs are damaged, and MHCs do not naturally regenerate in humans. Currently, there is no way to artificially regenerate MHCs. Cochlear implants and hearing aides are the only ways to treat hearing loss.

Thus, it would be advantageous to regenerate MHCs in a way to treat or reverse hearing loss or other problems associated with damaged MHCs.

SUMMARY

In one embodiment, a method of transforming human cells into mechanosensory hair cells (MHCs), such as inner hear hair cells in the cochlea and vestibular organs, can include: causing human Wharton's jelly cells (hWJCs) to increase expression of or biological function of HATH1 so as to transform the hWJCs into MHCs. In one aspect, the method can include administering a nucleic acid that encodes HATH1 to the hWJCs. In one aspect, the method can include causing inhibited expression of or biological function of HES1 and/or HES5 in the hWJCs. In one aspect, the method can include administering a nucleic acid that inhibits HES1 and/or a nucleic acid that inhibits HES5 to the hWJCs. In one aspect, the method can include causing inhibited expression of or biological function of HES1 and/or HES5 in the WJCs by administering a nucleic acid that inhibits HES1 and/or a nucleic acid that inhibits HES5. In one aspect, one of more of the nucleic acids are administered to the WJCs by non-viral nucleic acid delivery. In one aspect, the non-viral nucleic acid delivery is electroporation. In one aspect, the nucleic acid that encodes HATH1 includes a sequence of SEQ ID NO: 2; the nucleic acid that inhibits HES1 includes a sequence of SEQ ID NO: 3; and the nucleic acid that inhibits HES5 includes a sequence of SEQ ID NO: 4.

In one embodiment, the method is devoid of administering a nucleic acid that encodes MATH1.

In one embodiment, the method can include seeding the transforming hWJCs or MHCs onto a substrate shaped as a cochlea and/or vestibular organs. In one aspect, the substrate is a decellularized cochlea and/or vestibular organs. In one aspect, the method can include perfusing the transforming hWJCs or MHCs onto the decellularized cochlea and/or vestibular organs.

In one aspect, the transforming of the hWJCs to the MHCs occurs within 7 days. That is, upon initiation of transformation, such transformation results in MHCs within 7 days. As such, biomarkers of MHCs can be detected within 7 days of the initiation of the transformation from hWJCs.

In one embodiment, a method of providing mechanosensory hair cells (MHCs) to an inner ear of a subject can include: causing human Wharton's jelly cells (hWJCs) to increase expression of or biological function of HATH1 so as to transform the hWJCs into MHCs; and implanting the MHCs into the inner ear of the subject. In one aspect, the implanted MHCs are sufficient to improve hearing and/or balance in the subject. The generated MHCs can be implanted into a cochlea and/or vestibular organs of a subject, such as a subject in need thereof. The subject may have hearing loss or balance problems.

In one aspect, a cell culture system can include: a decellularized cochlea and/or vestibular organs; and mechanosensory hair cells (MHCs) growing on the decellularized cochlea and/or vestibular organs. In one aspect, the MHCs are characterized as being derived from human Warton's jelly cells (WJCs) that have been transfected with a nucleic acid that encodes HATH1 and a nucleic acid that inhibits HES1 and a nucleic acid that inhibits HES5. In one aspect, the one or more test substances in the MHCs include one or more test substances that are not native to Warton's jelly cells (WJCs) or MHCs and that are present in an amount to screen for biological activity thereof.

In one embodiment, a method of screening compounds for biological activity on mechanosensory hair cells (MHCs) can include: providing the system having a decellularized cochlea and/or vestibular organs and mechanosensory hair cells (MHCs) growing on the decellularized cochlea and/or vestibular organs; administering a test substance to the MHCs; and determining whether or not the test substance has biological activity on the MHCs. In one aspect, the test substance is determined to have a negative biological activity on the MHCs, and the method can include: selecting the test substance for further testing of toxicity of the test substance on MHCs. In one aspect, the test substance is determined to have a positive biological activity on the MHCs, and the method can include: selecting the test substance for further testing of therapeutic benefit for treatment of hearing and/or balance loss.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

Figure 1:
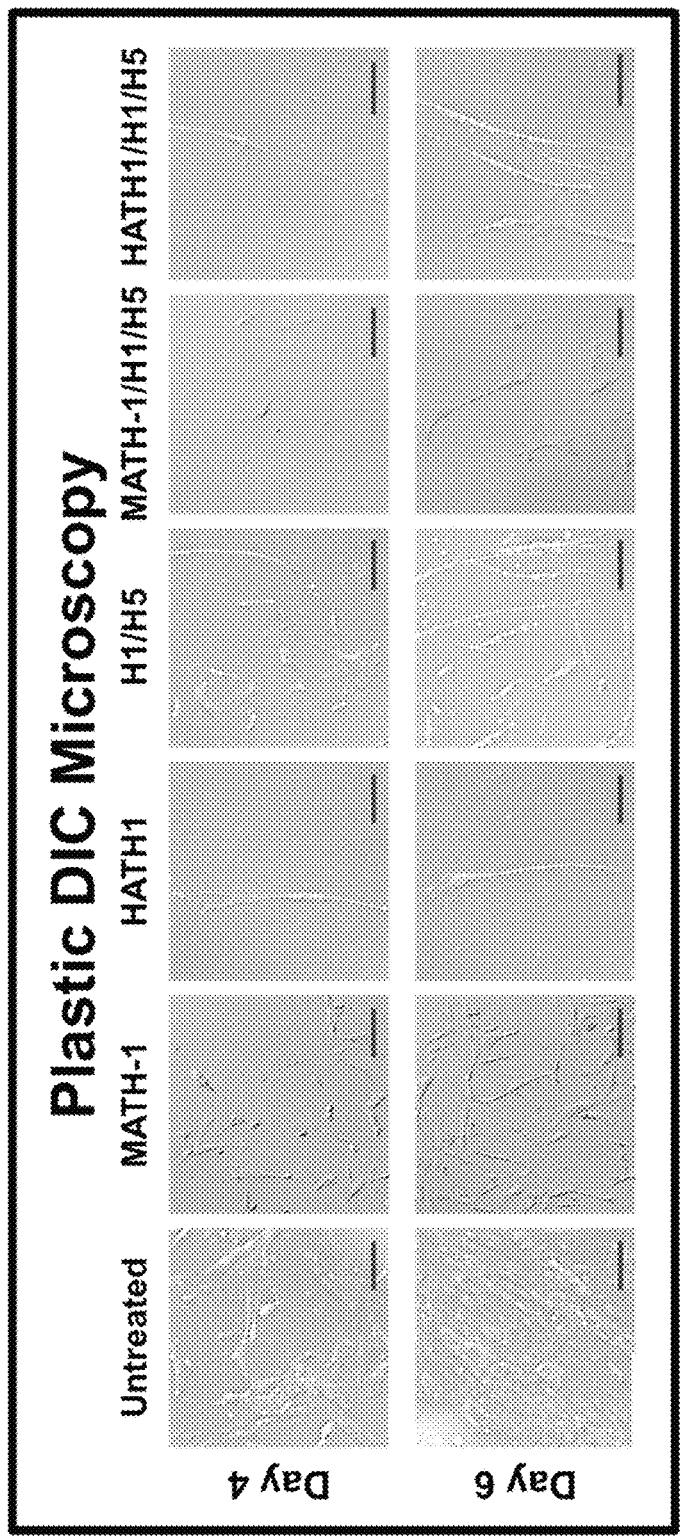
FIG. 1 includes micrographs of hWJC cells after various treatments with MATH1, HATH1, HES1, and/or HES2.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

In one embodiment, the present invention includes compositions, systems, and methods for reprogramming of human Wharton's Jelly cells (WJCs) to develop and behave as mechanosensory hair cells (MHCs), and thereby such reprogrammed WJCs can be generated MHCs. Such generation of MHCs can be through different techniques. In one example, genetic manipulation of the NOTCH signaling genes in WJCs can cause increased expression for HATH1, and silenced or reduced expression for HES1 and HES5 to form the MHCs. In another example, culturing of WJCs (e.g., hWJCs) in a 3D system that mimics the native MHC environment, such as a decellularized cochlea and/or vestibular organs, can form MHCs.

In one aspect, HATH1 can be upregulated in WJCs without down-regulation by HES1 and HES5 to form MHCs. In another aspect, a gene encoding HATH1 can be administered to the WJCs along with siRNA or other silencing RNA to down-regulate HES1 and HES5 to form the MHCs. For example, HATH1 can be over-expressed by delivering HATH1 plasmid DNA to target cells, such as hWJCs, thus increasing the atonal effect and the potential for MHC development. At the same time, HES1 and HES5 gene expression can be suppressed by delivering siRNA against HES1 and siRNA against HES5, which can further increase the atonal effect and the potential for MHC development. In one aspect, the methodology of producing MHCs can include delivering HATH1 plasmid DNA to hWJCs using any delivery method, such as viral, non-viral polymers, or any other non-viral method, such as electroporation or precipitation, where a non-viral delivery method can be preferred. In another aspect, the methodology of producing MHCs can include delivering HES1 siRNA and HES5 siRNA to hWJCs using any delivery method, where a non-viral method can be preferred, such as electroporation. In one aspect, the methodology for producing MHCs can include simultaneously increasing HATH1 expression via non-viral delivery of HATH1 plasmid DNA and suppressing HES1 and HES5 expression by the non-viral delivery of siRNA against HES1 and siRNA against HES5. The non-viral delivery of the HATH1 plasmid DNA and HES1 and HES5 siRNA can be done simultaneously with the same non-viral delivery method.

In one embodiment, the present invention can include using a cochlea, such as a decellularized cochlea and/or vestibular organs, as a substrate for growing the WJCs into MHCs. Also, the present invention can include using a cochlea to investigate the role the physical architecture of the cochlea plays in the development and maintenance of MHCs in the cochlea, which can be done ex-vivo or in-vitro. Furthermore, the extracellular matrix of the cochlea and/or vestibular organs can be used for a substrate for growing WJCs into MHCs, or using such extracellular matrix to investigating the role the extracellular matrix plays in the development, maintenance, and repair of MHCs. In one aspect, the methodology can include seeding WJCs (e.g., hWJCs) on top of a decellularized cochlea and/or vestibular organs, such as a human, dog, rat, mouse, or other cochlea and/or vestibular organs. The methodology can include seeding WJCs, such as hWJCs, which have been transfected with HATH1 plasmid DNA on top of a decellularized cochlea (e.g., mouse) and/or vestibular organs. Additionally, the methodology can include seeding WJCs, such as hWJCs, which have been transfected with siRNA against HES1 and siRNA against HES5 on top of a decellularized mouse cochlea and/or vestibular organs. Accordingly, HATH1 up-regulation can be induced with or without HES1 and/or HES5 down-regulation, and HES1 and/or HES5 down-regulation can be induced with or without HATH1 up-regulation. In one aspect, only one of HES1 or HES5 needs to be down-regulated with or without up-regulation of HATH1. However, in one aspect, the methodology can include seeding hWJCs that have been transfected with HATH1 plasmid DNA, siRNA against HES1, and siRNA against HES5 on top of a decellularized cochlea (e.g., mouse) and/or vestibular organs.

In one embodiment, the methodology can include perfusing the hWJCs into a decellularized cochlea and/or vestibular organs. In one aspect, this can include perfusing hWJCs that have been transfected with HATH1 plasmid DNA into a decellularized cochlea. In one aspect, the methodology can include perfusing hWJCs that have been transfected with siRNA against HES1 and siRNA against HES5 into a decellularized cochlea. In one aspect, the methodology can include perfusing hWJCs that have been transfected with HATH1 plasmid DNA, siRNA against HES1, and siRNA against HES5 into a decellularized cochlea. While decellularized mouse cochlea has been used and described, any mammal decellularized cochlea can be used.

Culturing the WJCs in a decellularized cochlea provides several advantages. For example, the WJCs can be cultured in a 3D environment that physically and mechanically mimics the environment in which MHCs develop. The WJCs seeded on cochleae can be studied in real-time outside of the body. The use of cochleae as scaffolds provides a culturing system that is both 3D and flexible in design. Different cell types or cells with different treatments can be seeded in combination or individually into the cochlea, enabling the study of a more advanced system for MHC and sensory epithelium development. Also, using the cochlea shape as a 3D culture system provides a template in the study of MHC development and regeneration. A 3D culture system provides a means to examine how signaling pathways change when cells are cultured in an environment native to MHC and sensory epithelium instead of in 2D. This can also be done with vestibular organs.

In one aspect, the 3D culture system may be used to screen for potential ototoxic agents and therapeutic agents, which could accelerate the early-stage development of new treatments for damaged sensory epithelium. As such, hWJCs can be grown on a cochlea-shaped substrate and/or vestibular organs, and then treated to induce formation of MHC with or without test compounds to determine whether they promote or inhibit formation of the MHCs. Known screening methods can be performed to find hits for further study for effects in MHCs generation.

In one embodiment, the hWJCs can be manipulated to function similar to mesenchymal stem cells, and can be used in MHC regeneration. In a preferred manipulation, the process can include simultaneously increasing HATH1 expression while suppressing HES1 and HES5 expression. The extracellular matrix and architecture of the cochlea are widely thought not to be the primary components that affect MHC differentiation and maintenance. Thus, utilization of the extracellular matrix as an extracellular material for guiding stem cells toward a MHC phenotype as described herein is surprising and unexpected.

The hWJCs are similar to bone marrow stem cells, which means hWJCs are multipotent stem cells that can differentiate into any tissue originating from the mesoderm germ layer (e.g., cartilage, bone, fat, muscle, etc.). Thus, hWJCs are ideal for applications that focus on cartilage, bone, fat, or muscle regeneration. It was previously thought that hWJCs may not be able to differentiate any other tissue types that are not connective tissue or found in the mesoderm germ layer. The hWJCs were previously thought to not be able to differentiate down any other non-mesoderm lineages, and thus were previously considered to be not ideal for neuron applications or intestinal applications. HATH1 delivery to hWJCs to transform them to MHCs was surprising and unexpected.

When a cochlea tissue is decellularized, all that is left is the extracellular matrix with no biochemical signals. Thus, a decellularized cochlea tissue is an inert biomaterial to grow cells on. However, the cochlea has a very unique architecture, and the architecture and physical properties can play a role in development of MHCs. Thus, the hWJCs exhibited phenotypic markers exclusive to MHCs after being seeded on or perfused inside the decellularized cochlea. This can be the same for vestibular organs.

The transcription factor atonal homolog 1 (ATOH1) has multiple homologues that are functionally conserved between species and is responsible for the generation of sensory hair cells. To evaluate potential functional differences between homologues, human and mouse atho1 were delivered to human umbilical cord mesenchymal stromal cells from Wharton's jelly. Delivery of the human atonal homolog, HATH1, to human Wharton's jelly cells demonstrated superior expression of inner ear hair cell markers and characteristics compared to delivery of the mouse homolog, MATH1. Inhibition of HES1 and HES5 signaling further increased the potency of the atonal effect. Transfection of Wharton's jelly cells with HATH1 DNA, HES1 siRNA, and HES5 siRNA displayed positive identification of key hair cell and support cell markers found in the organ of Corti. In the first side-by-side evaluation of HATH1 and MATH1 in human cells, substantial differences were observed, suggesting that the two atonal homologues may not be interchangeable between species.

In one embodiment, by over-expressing a target gene (e.g., HATH1) for MHC differentiation in human umbilical cord mesenchymal stem cells (hUCMSCs)) also known as human Wharton's jelly cells (hWJCs), while using siRNA to block negative regulators (HES1 and HES5) of the target gene can generate neuronal-like cells similar to the vestibular-cochlear nerve. The cells can be referenced as as human Wharton's Jelly Cells (hWJCs), and referred to as human umbilical cord mesenchymal stem cells (hUCMSCs). After treating hUCMSCs with HATH1 pDNA and HES1 and HES5 siRNA, there were differences between treated hUCMSCs and untreated hUCMSCs. Over the course of 10 days, bright-field microscopy revealed distinct differences in the morphological character of cells from both groups. Untreated hUCMSCs remained spindle-like in shape over the course of 10 days. Treated hUCMSCs became elongated and developed synaptic-like processes over the course of 10 days. Four days after treatment, treated hUCMSCs displayed bipolar elongation. Membrane staining revealed that distinct populations of cells were immerging 24 hours after treatment. Treated hUCMSCs take up the dye much more strongly than untreated hUCMSCs. The membrane stain is a method used to identify actively firing neurons and cells with high metabolic activity at the cell membrane. Over the course of 10 days, treated hUCMSCs continued to maintain a population with significantly increased membrane dye uptake as in comparison to the untreated hUCMSCs. Immunocytochemistry revealed the active protein expression of ATOH1 in treated hUCMSCs 24 hours after treatment, whereas untreated hUCMSCs did not reveal any ATOH1 protein expression. 10 Days after treatment, cell characterization via flow cytometry revealed that untreated hUCMSCs had maintained stem cell character, whereas treated hUCMSCs had started to shift away from established stem cell characterization parameters. Interestingly, both cell characterization via flow cytometry and gene expression via RT-qPCR revealed that while treated hUCMSCs moved away from the original stem cell phenotype, some of the treated hUCMSCs maintained high expression of a key pluripotent marker after treatment. Thus, based on the data hUCMSCs are responsive to treatment with HATH1 pDNA and HES1 and HES5 siRNA, and that such treatment has moved hUCMSCs toward an inner ear tissue phenotype. The treated hUCMSCs move toward what appears to be neuronal phenotype similar in character to the vestibular-cochlear nerve that transmits sensory information from IEHCs to the brain regarding balance and hearing.

In one aspect, HATH1 plasmid DNA delivered in combination with HES1 and HES5 siRNA to hUCMSCs can produce neuron-like cells. Using the plasmid DNA/siRNA combination for nucleic acid delivery has enabled creation of neuron-like cells efficiently and robustly. Thus, these neuron-like cell types may be used for drug screen testing, disease modeling, as tissue transplants, or any other biotechnological use.

In one embodiment, the methodology of generating MHCs can be used for treating sensorineural hearing loss, such as in mammals. The generated MHCs can be used to regenerate hair cells in the inner ear. Thus, the generated MHCs are able to renew and regenerate to repair damage. The generated MHCs can be obtained and then implanted in a subject. The generated MHCs can be obtained with or without the cochlea and/or vestibular organ substrates, and can be implanted with or without the cochlea and/or vestibular organ substrates. The implantation can be for therapies to treat or restore hearing loss or balance loss.

In one aspect, the generated MHCs can be implanted into inner ear epithelium, such as at the organ of Corti in the cochlea, and/or in the utricle and/or saccule in the vestibular organs. The generated MHCs can be implanted with or without the growth substrate. This can provide regenerated MHCs in precise quantities, types, and spacing of both hair cells (e.g., regenerated MHCs) and supporting cells to enable proper reception and transmission of neurosensory signals. This can be used for treatment of hearing loss or balance.

In one aspect, the generated MHCs can be used to partially or fully restore or repair inner ear sensory epithelium to a condition that is functionally similar or equivalent its original state. The methodology can be for generation of new hair cells without over-generation of hair cells. This can be used as to control the amount, density and distribution of the hair cells on the substrate. The generated MHCs can help improve hearing and/or balance after damage or have various other uses.

In one embodiment, ex-vivo or in-vitro generation of MHCs and then implantation, can overcome problems of using genetic manipulation in vivo that can result in over expression of ATOH1 in supporting cells. Such over expression of ATOH1 in supporting cells can unfavorably result in direct transdifferentiation, not regeneration. As such, the development of a MHC model outside the body may have a significant impact on further understanding how hair cells develop and are damaged, which may lead to new approaches for developing a therapy or a model for compound screening, such as to determine ototoxic drugs or other bioactive agents. The MEW model can be only generated MHCs or generated MHCs on decellularized cochlea and/or vestibular organs. Such MHC model can be studied in the presence of compounds (e.g., test substances) to determine if such compounds are ototoxic or have other bioactive properties. Also, the MHC model can be studied in the presence of compounds to determine if such compounds promote further improvement or inhibition of the MHCs.

In one embodiment, HATH1 transfected into hWJCs can result in cells that express critical markers associated with hair cells (e.g., MHCs) and neural epithelium. It is noted that MATH1 and HATH1 gene delivery in human cells has now been demonstrated that HATH1 expression differed from MATH1 expression in cells from human tissue, and HATH1 expression is superior for generating MHCs. In hWJCs, treatment with HATH1 displayed significant immediate increases in mRNA and protein expression of key hair cell markers, as compared to cells treated with MATH1, which displayed limited increases in gene expression and protein expression 1 day after transfection. The positive identity of GFAP in cells co-transfected with HATH1 and siRNA against HES1 and HES5 suggested an initial differentiation toward a neural-like phenotype. Myosin VIIa expression is expected if cells are differentiating toward a hair cell lineage, but HES5 expression is surprising, because HES5 encourages support cell differentiation by negatively regulating ATOH1, and thereby the results are surprising and unexpected. The positive expression of HES5 both at the gene and protein level suggested that hWJCs may be differentiating into both hair cells and supporting cells concurrently. The significant up-regulations GFI1 gene expression in cells co-transfected with HATH1 and siRNA against HES1 and HES5 suggest that presentation of a hair cell phenotype had started within at least a sub-population of treated cells. The gene expression and protein expression findings combined with the visual morphological changes in HATH1-transfected cells implied that some level of neuronal differentiation had taken place outside of the body, with limited stimulation by HATH1 and intercellular mediators of the NOTCH pathway. Accordingly, the presumption that atonal homologues are interchangeable between species is incorrect. This may be the case because the current study found that hWJCs showed increased gene, protein, and morphological features as well as increased viability when transfected with HATH1. In addition, transduction channels characteristic of hair cells and active neurons were implicated in the cell membranes of HATH1-transfected cells and cells co-transfected with HATH1 and siRNA against HES1 and HES5 based on the superior infiltration dye into hWJCs.

In one aspect, culturing treated cells in a three-dimensional environment similar to the native cochlea or co-culture of treated cells with a combination of native hair cells and support cells may further enhance the atonal effect and potential display of hair cell characteristics. The culturing can produce cells or tissues that can be implanted and may also be used for various treatments that can be improved by growing the MHCs in the natural locations.

In summary, the data revealed that hWJCs transfected with HATH1 displayed far superior expression of key hair cell markers in relation to presentation of mRNA transcripts, proteins, and morphological features in contrast to hWJCs transfected with MATH1. The development and presentation of hair cell markers were further enhanced when HATH1-transfected hWJCs were co-transfected with siRNA against HES1 and HES5. The current study demonstrated that hWJCs can be manipulated outside of a target tissue to produce a rare and complex phenotype that may aid in illuminating how hair cells develop in the human body.

In one embodiment, a method of increasing expression of inner ear hair cell markers in human cells can include: administering human atonal homolog HATH1 to human Wharton's jelly cells (hWJCs) so as to increase expression of inner ear hair cell markers in the hWJCs. In one aspect, the increased expression is compared to when administering mouse homolog MATH1 to hWJCs. In one aspect, atonal homolog HATH1 is administered in a plasmid and transfected into the hWJCs. Such a method can also include inhibiting HES1 and/or HES5 signaling. In one aspect, the method can include administering HES1 siRNA and/or HES5 siRNA to the hWJCs. In one aspect, the method can include transfection of the hWJCs with HATH1 DNA, HES1 siRNA, and HES5 siRNA together. In one aspect, confirmation of the method being useful as described herein can include identification of hair cell and support cell markers found in organ of Corti.

In one embodiment, a method of inducing differentiation of umbilical cord stem cells to inner ear hair cells can include: administering human atonal homolog HATH1 to hWJCs so as to increase expression of inner ear hair cell markers in the hWJCs. In one aspect, the increased expression is compared to when administering mouse homolog MATH1 to hWJCs. In one aspect, atonal homolog hath1 is administered in a plasmid and transfected into the Wharton's jelly cells. In one aspect, the method can include inhibiting HES1 and HES5 signaling. In one aspect, the method can include administering HES1 siRNA and HES5 siRNA to the hWJCs. In one aspect, the method can include transfection of hWJCs with HATH1 DNA, HES1 siRNA, and HES5 siRNA. In one aspect, confirmation of the method being useful as described herein can include identification of hair cell and support cell markers found in organ of Corti.

EXPERIMENTAL

Human Wharton's jelly cells (hWJCs) were isolated from Wharton's jelly of five human umbilical cords.

Two PrecisionShuttle mammalian vectors with independent turboGFP expression from OriGene (Rockville, Md.) were used to deliver target genes to hWJCs. Cloning and verification services were provided by Blue Heron (Blue Heron Biotech LLC, Bothell, Wash.) to manufacture the vectors. In one vector, a MATH1 insert (NCBI GenBank ID: NM-007500.4, the sequence thereof incorporated herein by specific reference, SEQ ID NO: 1) was cloned in, and in the other vector a HATH1 insert (NCBI GenBank ID: U61148.1, the sequence thereof incorporated herein by specific reference, SEQ ID NO: 2) was cloned in. The MATH1 and HATH1 gene inserts were driven by a cytomegalovirus (CMV) promoter followed by a Kozak sequence, and the turboGFP gene was driven by a Simian virus 40 (SV40) promoter. The PrecisionShuttle vectors contained a Kanamycin resistance gene for bacterial selection.

Based on data (data not shown) custom HES1 siRNA (Hs_hes1_5, Gene Accession no.: NM_005524, Gene ID: 3280, the sequence thereof incorporated herein by specific reference, SEQ ID NO: 3) modified with 3'-Alexa Fluor 555 and custom HES5 siRNA (Hs_hes5_5, Gene Accession no.: NM_001010926, Gene ID: 388585, the sequence thereof incorporated herein by specific reference, SEQ ID NO: 4) modified with 3'-Alexa Fluor 647 (Qiagen) were selected for experiments.

All cells were suspended at a concentration of $5 \times 10^5$ cells per 100-µL solution at one of the five following ratios: 100 µL 4DNP1 (Untreated), 95 µL 4DNP1:5 µL MATH1 pDNA (1 µg per µL) (MATH1), 95 µL 4DNP1:5 µL HATH1 pDNA (1 µg per µL) (HATH1), 99 µL 4DNP1:0.5 µL HES1 siRNA (100 nM): 0.5 µL HES5 siRNA (100 nM) (H1/H5), 94 µL 4DNP1:5 µL MATH1 pDNA (1 µg per µL): 0.5 µL HES1 siRNA (100 nM): 0.5 µL HES5 siRNA (100 nM) (MATH1/H1/H5), 94 µL 4DNP1:5 µL HATH1 pDNA (1 µg per µL): 0.5 µL HES1 siRNA (100 nM): 0.5 µL HES5 siRNA (100 nM) (HATH1/H1/H5). The untreated control cells were not nucleofected and were immediately pipetted into 6-well plates (BD Biosciences) or Nunc™ Lab-Tek™ 8-well chambered coverglass slides (Thermo Scientific, Waltham, Mass.) pre-coated with Fibronectin (BD Biosciences) containing 1.5 mL or 0.5 mL, respectively, of 37° C. pre-warmed traditional hWJC medium. Cells were transfected in a 4D Nucleofector™ (Lonza) and nucleofected with the FF-104 program.

At 1, 3, and 7 days after transfection, cells were collected and harvested for gene expression analysis via real time quantitative polymerase chain reaction (RT-qPCR), and RNA was collected from each cell sample. RNA was converted to cDNA. Three replicates from each of five umbilical cords (n=5) were taken for gene expression analysis at 1, 3, and 7 days post transfection. Live cell fluorescent imaging and flow cytometry was performed. The hWJCs were collected for live stain imaging 24 hours after transfection. Cells from each cord were stained and imaged 7 days after transfection under a confocal microscope. At 1, 3, and 7 days after transfection, cells were collected for immunocytochemistry.

Primary antibodies were pre-conjugated to Quantum Dots (Qdot®) The following primary antibodies were conjugated to the following Qdots: Anti-human ATOH1 (Millipore, Billerica, Mass.) pre-conjugated to Qdot 525 (1:200; Life Technologies), Anti-human HES1 (Millipore) pre-conjugated to Qdot 565 (1:200; Life Technologies), Anti-human MYOSIN VIIa (Novus, Littleton, Colo.) pre-conjugated to Qdot 605 (1:500, Life Technologies), Anti-human HES5 (Millipore) pre-conjugated to Qdot 655 (1:200, Life Technologies), and Anti-human GFAP (Millipore) pre-conjugated to Qdot 800 (1:100, Life Technologies). Cells were imaged using confocal microscopy. Cells were collected from each umbilical cord at 1, 3, and 7 days after transfection and images were taken from individual wells on 8-well chambered glass slides.

Analysis of stem cell characteristics was performed. A sub-culture of cells from each cord was characterized through cell surface marker identification via flow cytometry. Primary cell surface antibodies and secondary antibodies were added sequentially one-at-a-time per incubation-wash cycle to avoid cross-reaction; however, pre-conjugated primary antibodies with secondary antibodies were added simultaneously. A single incubation-wash cycle consisted of adding a primary antibody, secondary fluorescent antibody, or primary antibody pre-conjugated to a specific fluorescent secondary antibody to the cell suspension. Cell surface marker antibodies and secondary antibodies were added in the following order at the following ratios: STRO-1 Mouse IgM (2.5:200) (1 mg per mL; R&D Systems, Minneapolis, Minn.); Alexa Fluor 568® Rabbit Anti-Mouse IgG (2:200) (2 mg per mL; Life Technologies); CD105 Mouse IgG (2.5:200) (1 mg per mL; R&D Systems); Qdot® 525 donkey anti-mouse IgG (2:200) (1 µM; Life Technologies); Human CD45 pre-conjugated to Qdot® 800 (2:200) (Life Technologies); Human CD73 pre-conjugated to FITC (5:200) (BD Biosciences); Human CD34 pre-conjugated to Brilliant Violet (5:200) (BD Biosciences); Human CD90 pre-conjugated to APC (5:200) (BD Biosciences). hWJCs were analyzed by flow cytometry on a MoFlo XDF FACS (Beckman Coulter). Positive identification of cell markers was defined as fluorescent emission that exceeded the fluorescent threshold of cells stained with corresponding isotype (negative) controls.

Cells transfected with HATH1 showed greater cell density than cells transfected with MATH1. hWJCs were transfected via Nucleofection™, an electroporative technique (Lonza, Basel Switzerland), with one of five different treatments: MATH1 pDNA, HATH1 pDNA, siRNA against HES1 and HES5, MATH1 pDNA and siRNA against HES1 and HES5, or HATH1 pDNA and siRNA against HES1 and HES5. At 24 hours post-transfection, there was a noticeable visual difference in cell numbers between cells treated with HATH1 versus cells treated with MATH1 (see Table 1). Twenty-four hours after transfection, flow cytometry revealed that there were 1.9 times more viable cells transfected with HATH1, and 2.2 times more viable cells transfected with HATH1 and siRNA against HES1 and HES5, than viable cells transfected with MATH1 (Table 1). In addition, 24 hours post-transfection cells co-transfected with HATH1 and siRNA against HES1 and HES5 displayed 3.7 times more viable cells than cells co-transfected with MATH1 and siRNA against HES1 and HES5. At 24 hours post-transfection, cells transfected with HATH1 displayed transfection efficiency that was 0.2 times greater than cells transfected with MATH1. Moreover, 7 days after transfection, cell counts revealed that there were 2.8 times more viable cells transfected with HATH1, and 3.1 times more viable cells transfected with HATH1 and siRNA against HES1 and HES5, than cells transfected with MATH1. At 7 days post-transfection cells co-transfected with HATH1 and siRNA against HES1 and hes5 displayed 2.8 times more viable cells than cells co-transfected with MATH1 and siRNA against HES1 and HES5.

Only cells transfected with HATH1 revealed significant visual changes in morphology. Visual morphological differences were evident between untreated control cells and cells treated with HATH1 and siRNA against HES1 and HES5 starting at Day 3 (see incorporated provisional application). Cells treated with MATH1 displayed a fibroblastic morphology, consistent with hWJCs. However, cells treated with HATH1, siRNA against HES1 and HES5, or a combination of both showed an elongated cell body with small projections expanding away from the cell body. Cells treated with both HATH1 and siRNA against HES1 and HES5 displayed a bipolar phenotype with cell extensions reaching out from the nucleus and terminating with multiple slender projections, uncharacteristic of hWJCs.

HATH1-transfected cells revealed infiltration of lipophilic dye. To further evaluate the development of morphological features of hair cells, controls and treatment groups were stained 7 days after transfection with a lipophilic dye that is known to enter cells through transduction channels found in hair cells and neurons. Cells treated with HATH1 stained positive for dye, as did cells treated with only siRNA against HES1 and HES5. Dye entered HATH1-transfected cells more readily and robustly than MATH1-transfected cells. Across cells from all five umbilical cords, we saw positive staining in the greatest quantities in cells treated with HATH1 only or HATH1 and HES1 siRNA and HES5 siRNA. The amount of positive staining varied between cells treated only with HATH1 and cells treated with HATH1 and siRNA against HES1 and HES5 (Table 2). Limited infiltration of dye was observed in some of the samples co-transfected with math1 and siRNA against HES1 and HES5 across cell samples from all five umbilical cords.

HATH1-transfected cells up-regulated different genes from MATH1-transfected cells. Gene expression was evaluated across all treated cells from all human umbilical cords at 1, 3, and 7 days after transfection. The common trend observed across all analyzed genes was an up-regulation of gene expression 1 day after transfection, and gene expression levels returned to levels similar to untreated controls 7 days after transfection (see incorporated provisional application). Gene expression in MATH1-transfected cells did not significantly differ from untreated control cells within the 7-day time period following transfection, except for JAGGED2, HES1, and HES5 genes, 1 day after transfection. Cells co-transfected with MATH1 and siRNA against HES1 and HES5 displayed no significant gene expression differences from untreated control samples within the 7-day time period following transfection. MATH1-transfected cells failed to show any significant increase in gene expression over the 7-day time period, whereas HATH1-transfected cells showed significant ($p<0.05$) increases in gene expression 1 day after transfection compared to untreated control cells in ATOH1 ($4.5\times10^5$ fold change), HES1 (6.8 fold change), HES5 (33.3 fold change), and MYOSIN VIIA (6.5 fold change). Cells that were co-transfected with HATH1 and siRNA against HES1 and HES5 displayed significant ($p<0.05$) increases in gene expression across ATOH1 ($3.2\times10^5$ fold change), HES5 (17.6 fold change), MYOSIN VIIa (11.0 fold change), GFI1 (2.9 fold change), and JAGGED2 (2.4 fold change) 1 day after transfection. HWJCs co-transfected with HATH1 and siRNA against HES1 and HES5 displayed significant ($p<0.05$) increases in gene expression across myosin VIIa (9.1 fold change) and JAGGED2 (1.2 fold change) 3 days after transfection.

Only Cells Transfected With HATH1 Displayed Prolonged Protein Expression of MYOSIN VIIa.

Cells were analyzed for protein expression via immunocytochemistry 1 day and 7 days after transfection (Table 3). All treated cells displayed positive identification of MYOSIN VIIa and HES5 1 day after transfection. However, cells co-transfected with HATH1 and siRNA against HES1 and HES5 displayed positive identification of glial fibrillary acidic protein (GFAP) 1 day after transfection. MATH1-transfected cells displayed a visual decrease in myosin VIIa and HES5 expression, whereas HATH1-transfected cells displayed a visual increase in immunostaining for myosin VIIa and HES5 7 days after transfection. No GFAP expression was detected in any treated group 7 days after transfection. Untreated control cells displayed no presentation of any hair cell marker proteins at 1 day or 7 days after culture.

The α-amino-3-hydroxy-5-methyl-4-isoxazolepropionic acid (AMPA) receptor was stained to identify active calcium permeable ion channels. MATH1-transfected cells and cells co-transfected with MATH1 and siRNA against HES1 and HES5 visually displayed limited presentation of the AMPA receptor, whereas HATH1-transfected cells, and cells co-transfected with HATH1 and siRNA against HES1 and HES5 displayed strong presentation of active AMPA receptors. Only minor changes in cell surface markers observed between untreated and treated cells.

The hWJCs were characterized for CD markers associated with stem cells 10 day after transfection and found no significant changes between untreated and treated cells. All cell populations were strongly negative for CD34 and CD45, which indicated that cell populations were non-hematopoietic. Additionally, all cell populations displayed presentation of CD73, CD90, and CD105, which are surface markers found on mesenchymal stem cells.

FIG. 1 shows that untreated hWJCs displayed a fibroblast-like morphology 4 days after plating. MATH-1-transfected hWJCs mostly displayed a fibroblastic morphology. The hWJCs transfected with HATH1 and/or siRNA against HES1 and HES5 displayed an elongated bipolar morphology 4 days after transfection, and multiple cell morphologies were observed 6 days after transfection, which included elongated bipolar morphologies, bulb-like morphologies, branching morphologies and select cells appeared to be "pear-shaped". Cell density steadily increased after transfection. Images were obtained using plastic differential interference contrast microscopy (PlasDIC) (Zeiss). Images are representative of cells from five different umbilical cords (n=5). MATH-1 represents cells transfected with MATH-1 pDNA. HATH1 represents cells transfected with HATH1 pDNA. H1/H5 represents cells transfected with HES1 and HES5 siRNA. MATH-1/H1/H5 represents cells co-transfected with MATH-1 pDNA, HES1 siRNA, and HES5 siRNA. HATH1/H1/H5 represents cells co-transfected with HATH1 pDNA, HES1 siRNA, and HES5 siRNA. Scale Bar=50 μm.

Figure 2:
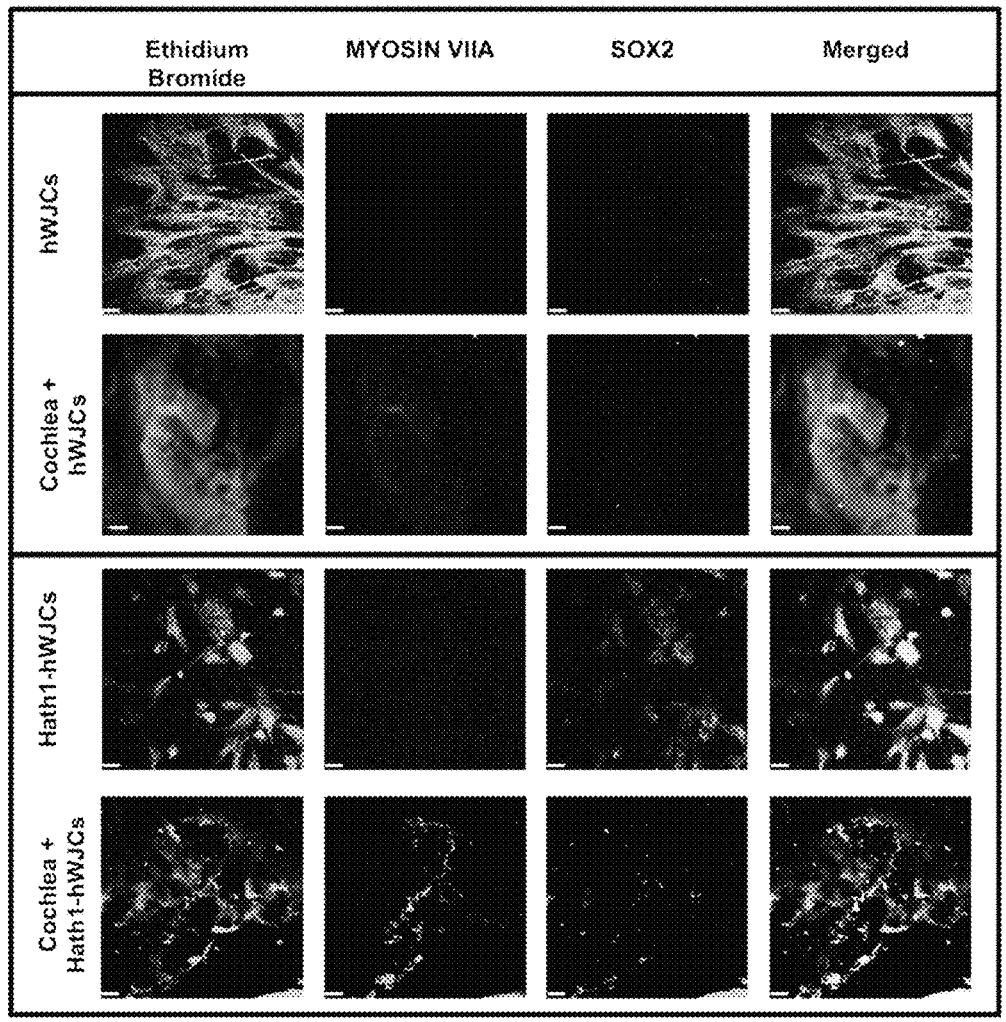
FIG. 2 includes micrographs of hWJC cultured on cochlear tissue.

FIG. 2 shows that even in the absence of any gene delivery, decellularized cochleae alone can induce expression of MYO7A and SOX2 in hWJCs within only 4 days. Untreated hWJCs cultured on fibronectin-coated glass showed no expression of MYO7A or SOX2 (Top Row). However, when untreated hWJCs were cultured in cochlear tissue from deceased C57BL/6 mice (Row 2), MYO7A was positively identified as well as SOX2. The decellularized cochlea also enhanced the differentiation of HATH1-transfected hWJCs toward the hair cell phenotype at 4 days. HATH1-transfected hWJCs grown on fibronectin-coated glass displayed positive presentation of MYO7A and SOX2 (Row 3). Remarkably, HATH1-transfected hWJCs showed an intense presentation of MYO7A and little SOX2 presentation when cultured in cochlear tissue (Row 4). Cell nuclei were stained with Ethidium Bromide (Blue). Cells were immunostained for MYO7A (Green), a motor protein found on stereocilia in hair cells, and SOX2 (Red), a marker for neuronal lineage commitment usually up-regulated before hair cell differentiation. MYO7A=myosin VIIA, scale bar=20 μm.

The cochlea substrate for seeding with cells can decellularized. Such decellularization can include: dissection of mouse carcass and removal of bulba; isolation of inner ear organs and soak the same with antibiotic solution; decellularize the organs with 1% SDS; decalcify with 10% EDTA. This process results in decellularized cochlea that can be seeded with WJCs that can be transformed into MHCs using the processes described herein.

Both untreated hWJCs and transfected hWJCs displayed varying presentations of MHC and neuron markers after only seven days of culture within decellularizied mouse cochleae.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims. All references recited herein are incorporated herein by specific reference in their entirety.

Tables

TABLE 1

Cell Viability

| Time Point | Untreated | MATH1 | HATH1 | siHES1/ siHES5 | MATH1/ siHES1/ siHES5 | HATH1/ siHES1/ siHES5 |
|---|---|---|---|---|---|---|
| Day 1 | 86.7 ± 5.6% | 57 ± 49% | 49 ± 30% | 72 ± 13% | 32 ± 41% | 49 ± 29% |
| Day 3 | 78 ± 36% | 55 ± 16% | 60 ± 15% | 80.2 ± 7.2% | 44 ± 18% | 63 ± 16% |
| Day 7 | 66 ± 13% | 69 ± 19% | 66 ± 11% | 80 ± 12% | 52 ± 20% | 68 ± 27% |

Percentages represented as the total number of viable cells out of entire population assessed. Values are represented as mean with standard deviation taken from cell populations from 5 different donors (n = 5)

TABLE 2

Identification of Transduction Channels via Lipophilic FM ® 1-43 Staining

| Donor Population | Untreated | MATH1 | HATH1 | siHES1/ siHES5 | MATH1/ siHES1/ siHES5 | HATH1/ siHES1/ siHES5 |
|---|---|---|---|---|---|---|
| A | − | − | + | + | − | ++ |
| B | − | − | ++ | + | − | + |
| C | − | − | + | + | − | ++ |
| D | − | − | ++ | + | − | ++ |
| E | − | − | ++ | + | − | + |

− = Negative detection of FM ® 1-43 Staining; + = positive detection FM ® 1-43 Staining; ++ strong positive detection of FM ® 1-43 staining.

TABLE 3

Identification of Hair Cell Marker MYO7A

| Donor Population | Untreated | MATH1 | HATH1 | siHES1/ siHES5 | MATH1/ siHES1/ siHES5 | HATH1/ siHES1/ siHES5 |
|---|---|---|---|---|---|---|
| Day 1 | − | + | + | + | + | + |
| Day 7 | − | − | ++ | − | + | ++ |

− = Negative presentation of MYO7A; + = positive presentation MYO7A; ++ strong positive presentation of MYO7A.

TABLE 4

Presentation of Hair Cell and Neuron Markers 7 Days Post-Transfection

| | Markers | DC | DC-Untreated hWJCs | DC-GFP | DC-HATH1 | DC-siHES1/ siHES5 | DC-HATH1/ siHES1/ siHES5 |
|---|---|---|---|---|---|---|---|
| Hair Cell | Actin | − | ++ | ++ | ++ | + | + |
| | MYO7A | − | ++ | + | ++ | + | ++ |
| Neuron | NEUROG1 | − | + | + | ++ | + | + |

− = Negative presentation; + = positive presentation; ++ strong positive presentation. DC = Decellularized Cochlea; hWJCs = human Wharton's jelly cells; GFP = Green Fluorescent Protein; HATH1 = Cells transfected with HATH1; siHES1 = siRNA against HES1; siHES5 = siRNA against HES5.

The invention claimed is:

1. A cell culture system comprising:
a decellularized cochlea; and
mechanosensory hair cells (MHCs) growing on and/or inside the decellularized cochlea, wherein the MHCs have an exogenous nucleic acid that encodes HATH1 and a promoter operably linked with the encoded HATH1.

2. The cell culture system of claim 1, comprising one or more test substances in the MHCs, the one or more test substances are not native to Wharton's jelly cells (WJCs) or MHCs and are present in an amount to screen for biological activity thereof.

3. The cell culture system of claim 2, comprising the MHCs having a nucleic acid that inhibits HES1.

4. The cell culture system of claim 2, comprising the MHCs having a nucleic acid that inhibits HES5.

5. The cell culture system of claim 2, comprising the MHCs having a nucleic acid that inhibits HES1 and a nucleic acid that inhibits HES5.

6. The cell culture system of claim 1, wherein the exogenous nucleic acid that encodes HATH1 includes a sequence of SEQ ID NO: 2.

7. The cell culture system of claim 3, wherein the nucleic acid that inhibits HES1 includes a sequence of SEQ ID NO: 3.

8. The cell culture system of claim 4, wherein the nucleic acid that inhibits HES5 includes a sequence of SEQ ID NO: 4.

9. The cell culture system of claim 2, wherein the decellularized cochlea is shaped as a cochlea.

10. The cell culture system of claim 2, comprising the MHCs devoid of a nucleic acid that encodes MATH1.

11. The cell culture system of claim 2, comprising human Wharton's jelly cells (WJCs).

12. The cell culture system of claim 2, wherein at least one of the one or more test substances is toxic to the MHCs so as to be capable of causing hearing and/or balance loss.

13. The cell culture system of claim 2, wherein at least one of the one or more test substances is therapeutic for treatment of hearing and/or balance loss.

14. The cell culture system of claim 2, wherein at least one of the one or more test substances is ototoxic.

15. The cell culture system of claim 2, wherein at least one of the one or more test substances promote formation of the MHCs.

16. The cell culture system of claim 2, further comprising neuron-like cell types.

17. The cell culture system of claim 1, wherein the exogenous nucleic acid is a plasmid DNA.

* * * * *

SEQUENCE LISTING

<160> NUMBER OF SEQ ID NOS: 4

<210> SEQ ID NO 1
<211> LENGTH: 2118
<212> TYPE: DNA
<213> ORGANISM: Mus musculus

<400> SEQUENCE: 1

```
acctggtgtg cgatctccga gtgagagggg gagggtcaga ggaggaagga aaaaaaatca      60
gaccttgcag aagagactag gaaggttttt gttgttgttg ttcggggctt atccccttcg     120
ttgaactggg ttgccagcac ctcctctaac acggcacctc cgagccattg cagtgcgatg     180
tcccgcctgc tgcatgcaga agagtgggct gaggtaaaag agttggggga ccaccatcgc     240
catccccagc cgcaccacgt cccgccgctg acgccacagc cacctgctac cctgcaggcg     300
```

```
agagaccttc ccgtctaccc ggcagaactg tccctcctgg atagcaccga cccacgcgcc    360
tggctgactc ccactttgca gggcctctgc acggcacgcg ccgcccagta tctgctgcat    420
tctcccgagc tgggtgcctc cgaggccgcg gcgcccgggg acgaggctga cagccagggt    480
gagctggtaa ggagaagcgg ctgtggcggc ctcagcaaga gccccgggcc cgtcaaagta    540
cgggaacagc tgtgcaagct gaagggtggg gttgtagtgg acgagcttgg ctgcagccgc    600
cagcgagccc cttccagcaa acaggtgaat ggggtacaga agcaaaggag gctggcagca    660
aacgcaaggg aacggcgcag gatgcacggg ctgaaccacg ccttcgacca gctgcgcaac    720
gttatcccgt ccttcaacaa cgacaagaag ctgtccaaat atgagaccct acagatggcc    780
cagatctaca tcaacgctct gtcggagttg ctgcagactc ccaatgtcgg agagcaaccg    840
ccgccgccca cagcttcctg caaaaatgac caccatcacc ttcgcaccgc ctcctcctat    900
gaaggaggtg cgggcgcctc tgcggtagct ggggctcagc cagccccggg aggggcccg    960 agacctaccc cgcccgggcc ttgccggact cgcttctcag gcccagcttc ctctgggggt    1020
tactcggtgc agctggacgc tttgcacttc ccagccttcg aggacagggc cctaacagcg    1080
atgatggcac agaaggacct gtcgccttcg ctgcccgggg gcatcctgca gcctgtacag    1140
gaggacaaca gcaaaacatc tcccagatcc cacagaagtg acggagagtt ttccccccac    1200
tctcattaca gtgactctga tgaggccagt taggaaggca acagctccct gaaaactgag    1260
acaaccaaat gcccttccta gcgcgcggga agcccgtga caaatatccc tgcacccttt    1320 aattttttggt ctgtggtgat cgttgttagc aacgacttga cttcggacgg ctgcagctct    1380
tccaatcccc ttcctcctac cttctccttc ctctgtatgt agatactgta tcattatatg    1440
tacctttacg tggcatcgtt tcatggtcca tgctgccaat atgctgctaa aatgtcgtat    1500
ctctgcctct ggtctgggtt tcacttattt tataccttgg gagttcatcc ttgcgtgttg    1560
cgctcactca caaataaggg agttagtcaa tgaagttgtt tccccaactg cttgagaccc    1620
gcattgggta ctttactgaa cacggactat tgtgttgtta aaatgcaggg gcagataaga    1680
gtatctgtag agcttagaca ccaagtgtgt ccagcagtgt gtctagcgga cccagaatac    1740
acgcacttca tcactggccg ctgcgccgcc ttgaagaaac tcaactgcca atgcagagca    1800
acttttgatt ttaaaaacag ccactcataa tcattaaact cttttgcaaat gtttgttttt    1860 gcaaatgaaa attaaaaaaa aacatgtagt gtcaaaggca tttggtcaat tttattttgc    1920
tttgttaaca ttagaaaagt tatttattat tgcgtatttg gacccatttc tacttaattg    1980 ccttttttttt acattttcta ctcgagatcg ttttattttg attagcaaa tccagttgcc    2040 attgctttat gtatgtatgc tcttttacaa atgataaaat aaactcggaa aaaaaaaaa    2100 aaaaaaaaaa aaaaaaaa                                                 2118
```

<210> SEQ ID NO 2
<211> LENGTH: 1572
<212> TYPE: DNA
<213> ORGANISM: Homo sapiens
<220> FEATURE:
<221> NAME/KEY: modified_base
<222> LOCATION: (1497)..(1497)
<223> OTHER INFORMATION: a, c, t, g, unknown or other
<220> FEATURE:
<221> NAME/KEY: modified_base
<222> LOCATION: (1504)..(1504)
<223> OTHER INFORMATION: a, c, t, g, unknown or other
<220> FEATURE:
<221> NAME/KEY: modified_base
<222> LOCATION: (1526)..(1526)

<223> OTHER INFORMATION: a, c, t, g, unknown or other
<220> FEATURE:
<221> NAME/KEY: modified_base
<222> LOCATION: (1564)..(1564)
<223> OTHER INFORMATION: a, c, t, g, unknown or other

<400> SEQUENCE: 2

| | | | | | | |
|---|---|---|---|---|---|---|
| gtcctctgca | cacaagaact | tttctcgggg | tgtaaaaact | ctttgattgg | ctgctcgcac | 60 |
| gcgcctgccc | gcgccctcca | ttggctgaga | agacacgcga | ccggcgcgag | gaggggttg | 120 |
| ggagaggagc | gggggagac | tgagtggcgc | gtgccgcttt | ttaaaggggc | gcagcgcctt | 180 |
| cagcaaccgg | agaagcatag | ttgcacgcga | cctggtgtgt | gatctccgag | tgggtggggg | 240 |
| agggtcgagg | agggaaaaaa | aaataagacg | ttgcagaaga | gacccggaaa | gggccttttt | 300 |
| tttggttgag | ctggtgtccc | agtgctgcct | ccgatcctga | gcgtccgagc | ctttgcagtg | 360 |
| caatgtcccg | cctgctgcat | gcagaagagt | gggctgaagt | gaaggagttg | ggagaccacc | 420 |
| atcgccagcc | ccagccgcat | catctcccgc | aaccgccgcc | gccgccgcag | ccacctgcaa | 480 |
| cttttgcaggc | gagagagcat | cccgtctacc | cgcctgagct | gtccctcctg | gacagcaccg | 540 |
| acccacgcgc | ctggctggct | cccactttgc | agggcatctg | cacggcacgc | gccgcccagt | 600 |
| atttgctaca | ttccccggag | ctgggtgcct | cagaggccgc | tgcgcccgg | gacgaggtgg | 660 |
| acggccgggg | ggagctggta | aggaggagca | gcggcggtgc | cagcagcagc | aagagccccg | 720 |
| ggccggtgaa | agtgcgggaa | cagctgtgca | agctgaaagg | cggggtggtg | gtagacgagc | 780 |
| tgggctgcag | ccgccaacgg | gccccttcca | gcaaacaggt | gaatgggtg | cagaagcaga | 840 |
| gacggctagc | agccaacgcc | agggagcggc | gcaggatgca | tgggctgaac | cacgccttcg | 900 |
| accagctgcg | caatgttatc | ccgtcgttca | acaacgacaa | gaagctgtcc | aaatatgaga | 960 |
| ccctgcagat | ggcccaaatc | tacatcaacg | ccttgtccga | gctgctacaa | acgcccagcg | 1020 |
| gaggggaaca | gccaccgccg | cctccagcct | cctgcaaaag | cgaccaccac | caccttcgca | 1080 |
| ccgcggcctc | ctatgaaggg | ggcgcgggca | acgcgaccgc | agctgggct | cagcaggctt | 1140 |
| ccggagggag | ccagcggccg | accccgcccg | ggagttgccg | gactcgcttc | tcagccccag | 1200 |
| cttctgcggg | agggtactcg | gtgcagctgg | acgctctgca | cttctcgact | ttcgaggaca | 1260 |
| gcgccctgac | agcgatgatg | gcgcaaaaga | atttgtctcc | ttctctcccc | gggagcatct | 1320 |
| tgcagccagt | gcaggaggaa | aacagcaaaa | cttcgcctcg | gtcccacaga | agcgacgggg | 1380 |
| aattttcccc | ccattcccat | tacagtgact | cggatgaggc | aagttaggaa | ggtgacagaa | 1440 |
| gcctgaaaac | tgagacagaa | acaaaactgc | cctttcccag | tgcgcgggaa | gccccgnggt | 1500 |
| taangatccc | cgcacccttt | aatttnggct | ctgcgatggt | cgttgtttag | caacgacttg | 1560 |
| gctncagatg | gt | | | | | 1572 |

<210> SEQ ID NO 3
<211> LENGTH: 1475
<212> TYPE: DNA
<213> ORGANISM: Homo sapiens

<400> SEQUENCE: 3

| | | | | | | |
|---|---|---|---|---|---|---|
| gggatcacac | aggatccgga | gctggtgctg | ataacagcgg | aatcccccgt | ctacctctct | 60 |
| ccttggtcct | ggaacagcgc | tactgatcac | caagtagcca | caaatataa | taaaccctca | 120 |
| gcacttgctc | agtagttttg | tgaaagtctc | aagtaaaaga | gacacaaaca | aaaaattctt | 180 |
| tttcgtgaag | aactccaaaa | ataaaattct | ctagagataa | aaaaaaaaa | aaaggaaaa | 240 |
| tgccagctga | tataatggag | aaaaattcct | cgtccccggt | ggctgctacc | ccagccagtg | 300 |

| | | |
|---|---|---|
| tcaacacgac accggataaa ccaaagacag catctgagca cagaaagtca tcaaagccta | 360 | |
| ttatggagaa aagacgaaga gcaagaataa atgaaagtct gagccagctg aaaacactga | 420 | |
| tttttggatgc tctgaagaaa gatagctcgc ggcattccaa gctggagaag gcggacattc | 480 | |
| tggaaatgac agtgaagcac ctccggaacc tgcagcgggc gcagatgacg gctgcgctga | 540 | |
| gcacagaccc aagtgtgctg gggaagtacc gagccggctt cagcgagtgc atgaacgagg | 600 | |
| tgacccgctt cctgtccacg tgcgagggcg ttaataccga ggtgcgcact cggctgctcg | 660 | |
| gccacctggc caactgcatg acccagatca atgccatgac ctaccccggg cagccgcacc | 720 | |
| ccgccttgca ggcgccgcca ccgccccac cgggacccgg cggcccccag cacgcgccgt | 780 | |
| tcgcgccgcc gccgccactc gtgcccatcc ccggggcgc ggcgcccct cccggcggcg | 840 | |
| cccctgcaa gctgggcagc caggctggag aggcggctaa ggtgtttgga ggcttccagg | 900 | |
| tggtaccggc tcccgatggc cagtttgctt cctcattcc caacggggcc ttcgcgcaca | 960 | |
| gcggccctgt catccccgtc tacaccagca acagcggcac ctccgtgggc cccaacgcag | 1020 | |
| tgtcaccttc cagcggcccc tcgcttacgg cggactccat gtggaggccg tggcggaact | 1080 | |
| gaggggggctc aggccacccc tcctcctaaa ctccccaacc cacctctctt ccctccggac | 1140 | |
| tctaaacagg aacttgaata ctgggagaga agaggacttt tttgattaag tggttacttt | 1200 | |
| gtgttttttt aatttctaag aagttactttt ttgtagagag agctgtatta agtgactgac | 1260 | |
| catgcactat atttgtatat attttatatg ttcatattgg attgcgcctt tgtattataa | 1320 | |
| aagctcagat gacatttcgt tttttacacg agatttctttt tttatgtgat gccaaagatg | 1380 | |
| tttgaaaatg ctcttaaaat atcttccttt ggggaagttt atttgagaaa atataataaa | 1440 | |
| agaaaaaagt aaaggctttt aaaaaaaaaa aaaaa | 1475 | |

<210> SEQ ID NO 4
<211> LENGTH: 1319
<212> TYPE: DNA
<213> ORGANISM: Homo sapiens

<400> SEQUENCE: 4

| | | |
|---|---|---|
| cgcgcttggc cttgcccgcg cccgctcgcc tcgtctcgcc cggcctcccc gcgtcgcctc | 60 | |
| gtcgcctgtt ccgcgccagg catggccccc agcactgtgg ccgtggagct gctcagcccc | 120 | |
| aaagagaaaa accgactgcg gaagccggtg gtggagaaga tgcgccgcga ccgcatcaac | 180 | |
| agcagcatcg agcagctgaa gctgctgctg gagcaggagt tcgcgcggca ccagcccaac | 240 | |
| tccaagctgg agaaggccga catcctggag atggctgtca gctacctgaa gcacagcaaa | 300 | |
| gccttcgtcg ccgccgccgg ccccaagagc ctgcaccagg actacagcga aggctactcg | 360 | |
| tggtgcctgc aggaggccgt gcagttcctg acgctccacg ccgccagcga cacgcagatg | 420 | |
| aagctgctgt accacttcca gcggcccccg gccgcgcccg ccgcgcccgc caaggagccc | 480 | |
| aaggcgccgg cgccgcgcc cccgcccgcg ctctccgcca aggccaccgc cgccgccgcc | 540 | |
| gccgcgcacc agcccgcctg cggcctctgg cggccctggt gacccggcgg gacctgcggg | 600 | |
| cgcgcggccc gacgaccaga gggcgagcct gctcctctcg cctgtaggga agcgccttcc | 660 | |
| cgccgtcgtc cgccccgggc ttggacgcgc ccttctccgg aaggctctgg ccccaagctg | 720 | |
| gccggcccgc aggagcccca ttctcagaga atgtgtgtgc agagtccctg ccgttttagg | 780 | |
| acaatcaggg cccatcttct gccaagtgtc tgacccatg gggttgttct gtgtttgcat | 840 | |
| ttaagcaagt gacttctggg aagtccccgg ccgcccgggg ttctatgata tttgtagtgc | 900 | |

-continued

```
cggggctcgc acactgctgc ccccagcctg tagaggactt tcttcagggc ccgtagctgc    960
tgggcgtacc cctggcaggc gggctgtgcc gcgggcacat ttgcctttg tgaaggccga    1020 actcgagctg tatcctcata ggaaacagtg atcacccgg acgggcgtcc aggaccctga    1080
gggccatggc caaaaggctc ctgagtgtgc ctggtggtct ggctggggct cacggtgggc    1140
tgtctgggga gggtgggtgc ctccactatg atccttaaag gattcctctg tgtgggtgga    1200
tgcgtgtggg cacgactttg tactcagaaa ttgaactctc agtcacgtgg aagccacggg    1260
actgctccga agccgccata ataaaatctg attgttcagc ccccaaaaaa aaaaaaaaa    1319
```